United States Patent
Park et al.

(10) Patent No.: US 10,740,017 B2
(45) Date of Patent: Aug. 11, 2020

(54) DYNAMIC MEMORY PROTECTION

(71) Applicant: QUALCOMM Incorporated, San Diego, CA (US)

(72) Inventors: Chando Park, Palo Alto, CA (US); Wei-Chuan Chen, San Diego, CA (US); Sungryul Kim, San Diego, CA (US); Adam Edward Newham, Poway, CA (US); Seung Hyuk Kang, San Diego, CA (US); Rashid Ahmed Akbar Attar, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 107 days.

(21) Appl. No.: 15/963,668

(22) Filed: Apr. 26, 2018

(65) Prior Publication Data

US 2019/0332306 A1 Oct. 31, 2019

(51) Int. Cl.
| | |
|---|---|
| *G06F 3/06* | (2006.01) |
| *G11C 11/00* | (2006.01) |
| *G11C 29/52* | (2006.01) |
| *A61N 1/372* | (2006.01) |
| *H04W 4/80* | (2018.01) |

(52) U.S. Cl.
CPC ....... *G06F 3/0647* (2013.01); *A61N 1/37223* (2013.01); *G06F 3/0619* (2013.01); *G06F 3/0685* (2013.01); *G11C 11/005* (2013.01); *G11C 29/52* (2013.01); *H04W 4/80* (2018.02)

(58) Field of Classification Search
CPC .... G06F 3/0647; G06F 3/0619; G06F 3/0685; G11C 11/005; G11C 29/52
See application file for complete search history.

(56) References Cited

U.S. PATENT DOCUMENTS

| | | | |
|---|---|---|---|
| 2007/0153572 A1* | 7/2007 | Boeve | G11C 11/15 365/171 |
| 2010/0198280 A1* | 8/2010 | Comdorf | A61N 1/37276 607/3 |
| 2010/0249881 A1* | 9/2010 | Comdorf | A61N 1/37276 607/60 |
| 2016/0078907 A1* | 3/2016 | Woo | G11C 7/04 711/162 |

* cited by examiner

*Primary Examiner* — Ramon A. Mercado
(74) *Attorney, Agent, or Firm* — Patterson & Sheridan, LLP

(57) ABSTRACT

Aspects of the present disclosure relate to protecting the contents of memory in an electronic device, and in particular to systems and methods for transferring data between memories of an electronic device in the presence of strong magnetic fields. In one embodiment, a method of protecting data in a memory in an electronic device includes storing data in a first memory in the electronic device; determining, via a magnetic sensor, a strength of an ambient magnetic field; comparing the strength of the ambient magnetic field to a threshold; transferring the data in the first memory to a second memory in the electronic device upon determining that the strength of the ambient magnetic field exceeds the threshold; and transferring the data from the second memory to the first memory upon determining that the strength of the ambient magnetic field no longer exceeds the threshold.

20 Claims, 3 Drawing Sheets

DYNAMIC MEMORY PROTECTION

INTRODUCTION

Aspects of the present disclosure relate to protecting the contents of memory in an electronic device, and in particular to systems and methods for transferring data between memories of an electronic device in the presence of strong magnetic fields.

Electronic devices generally include a memory for storing and manipulating data in concert with a processor. As electronic devices get smaller, faster, and more capable, the demands on the core components of the devices, such as the memory, grow accordingly. For example, electronic devices are evolving to use lower power memory technologies (and others) in order to extend their operational capabilities.

Magnetoresistive random access memory (MRAM) is one such technology that is evolving to provide increased performance, which leads to new applications of the technology, such as in body-implantable devices (e.g., within a human body). However, because such implantable devices may not be easily separated from the body in which they reside, the implantable devices may be subjected to certain environmental conditions that are detrimental to their performance, such as strong magnetic fields. For example, if a human host of an implantable device needs to undergo a magnetic resonance imaging (MRI) scan, the magnetic-based memory may lose its content by the strong magnetic fields created by the MRI machine. For life-critical applications (e.g., pacemakers), this presents a significant problem that may prevent such magnetic-based memories from being used in implantable devices—or any other electronic devices that may experience strong magnetic field environments. This is particularly unfortunate when a magnetic-based memory may otherwise be the best performance option for the device.

Accordingly, there is a need for systems and methods to implement magnetic-based memory technologies in electronic devices that may be subjected to strong magnetic fields.

BRIEF SUMMARY

Certain embodiments provide a method of protecting data in a memory in an electronic device, including: storing data in a first memory; receiving, from a remote device via a data transmission protocol, a first indication of an intensity of an ambient magnetic field; comparing the first indication of the intensity of the ambient magnetic field to a threshold; transferring the data in the first memory to a second memory upon determining that the first indication of the intensity of the ambient magnetic field exceeds the threshold; receiving, from the remote device via the data transmission protocol, a second indication of the intensity of the ambient magnetic field; comparing the second indication of the intensity of the ambient magnetic field to the threshold; and transferring the data from the second memory to the first memory upon determining that the second indication of the intensity of the ambient magnetic field no longer exceeds the threshold.

Other embodiments provide an electronic device, including: a first memory; a second memory; a transceiver; and a processor in data communication with the first memory, the second memory, and the transceiver and configured to: store data in the first memory; receiving, from a remote device via the transceiver using a data transmission protocol, a first indication of an intensity of an ambient magnetic field; compare the first indication of the intensity of the ambient magnetic field to a threshold; transfer the data in the first memory to a second memory upon determining that the first indication of the intensity of the ambient magnetic field exceeds the threshold; receive, from the remote device via the transceiver using the data transmission protocol, a second indication of the intensity of the ambient magnetic field; compare the second indication of the intensity of the ambient magnetic field to the threshold; and transfer the data from the second memory to the first memory upon determining that the second indication of the intensity of the ambient magnetic field no longer exceeds the threshold.

Other embodiments provide a non-transitory, computer-readable medium comprising instructions that, when executed by a processor of an electronic device, cause the electronic device to perform a method of protecting data in a memory in an electronic device, the method comprising:

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
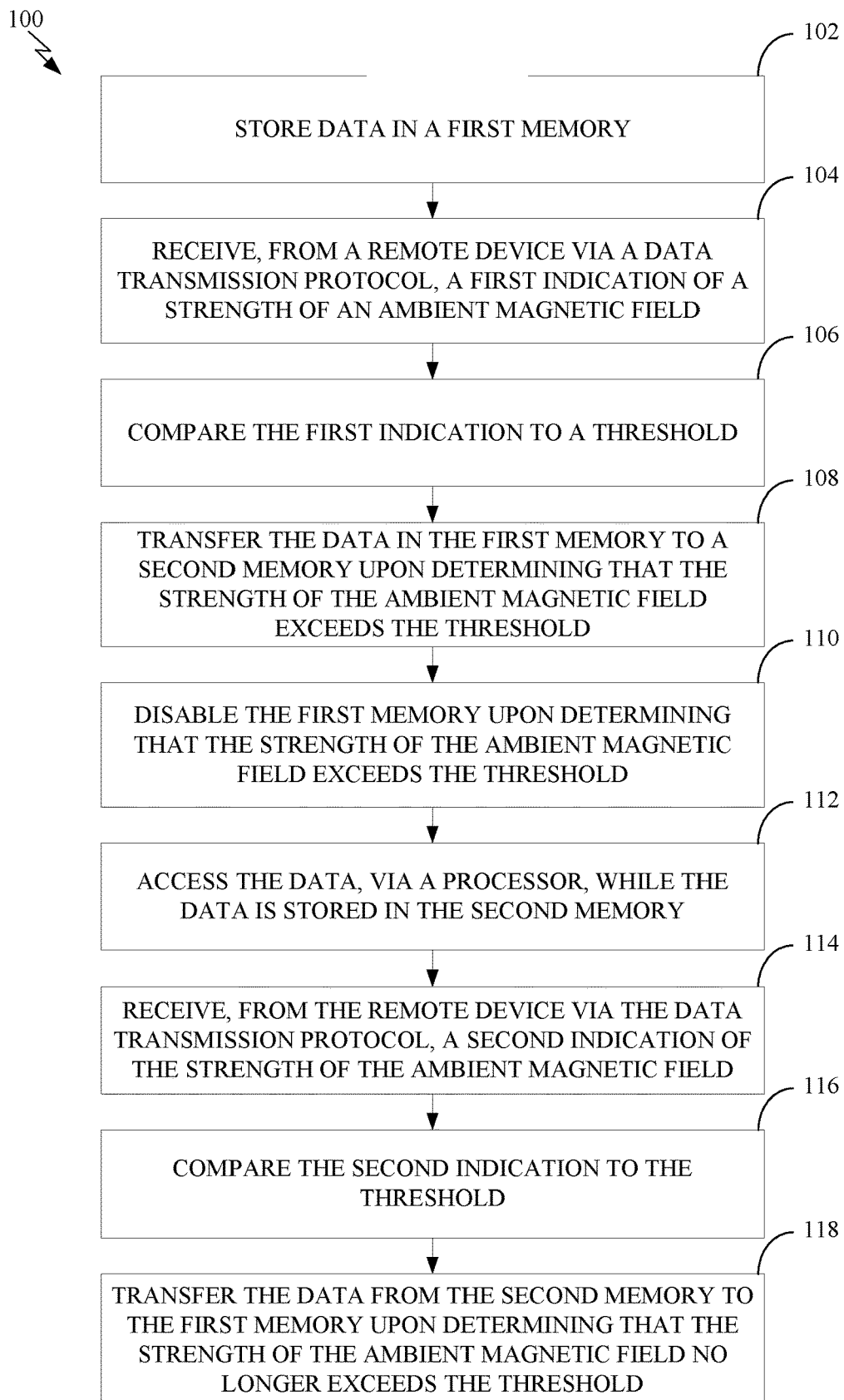
FIG. 1 depicts a method of protecting data in a memory in an electronic device.

Aspects of the present disclosure provide methods and apparatuses for protecting the contents of memory in an electronic device, in particular for transferring data between memories of an electronic device in the presence of strong magnetic fields.

The following description provides examples, and is not limiting of the scope, applicability, or embodiments set forth in the claims. Changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

Implantable electronic devices (e.g., medical devices implanted into a human body) have become far more capable and practical as a byproduct of improved electronic technologies, such as improved memory technologies that both store more data in a smaller size and use less power while doing so. An emerging low-power, high-performance memory technology is magnetoresistive random access memory (MRAM). While magnetic-based memories are not new, new architectures for magnetic-based memory are emerging that offer significant performance improvements over existing technologies.

For example, Spin-Transfer Torque (STT) MRAM is a new, non-volatile magnetic-based RAM architecture that is well-suited for many electronic device applications because it delivers the high-performance of existing memory technologies, like dynamic random-access memory (DRAM) and static random-access memory (SRAM), while offering additional benefits, such as low power, endurance, space efficiency, and scalability. For example, STT-MRAM does not require a power-refresh like DRAM, and the read process is not destructive, which collectively leads to lower power use and latency in the electronic device. As another example, STT-MRAM cells generally use one transistor as compared to the four or six transistors in a typical SRAM, which saves space and power in operation. Further, STT-MRAM scales well with decreasing device sizes and is compatible with existing CMOS manufacturing processes. This and other technological developments to STT-MRAM make it an ideal replacement for SRAM, DRAM, and NOR-flash in electronic devices. Thus, STT-MRAM is an excellent candidate for implantable electronic devices where size, power efficiency, and capability are all at a premium.

Generally, an MRAM memory cell includes a magnetic tunnel junction (MTJ) for sensing the state of a memory cell. A recent development in MRAM technology is called the Perpendicular MTJ (pMTJ), where the magnetic moments are perpendicular to the silicon substrate surface. pMTJ-based STT-MRAM scales with smaller device sizes better than earlier versions of STT-MRAM, which, for example, used an in-plane MTJ (iMTJ).

While generally non-volatile, magnetic-based memories like STT-MRAM are sensitive to certain environmental conditions, such as strong magnetic fields. pMTJ based STT-MRAM may generally be immune to magnetic fields up to a strength (i.e., intensity) of 1,500 Oersteds (Oe), but may risk data loss in more intense magnetic field environments. As such, an STT-MRAM may risk data corruption or loss in the proximity of certain machinery, like a magnetic resonance imaging (MRI) machine. For example, many MRI systems operate at around 15,000 Oe (1.5 T), but commercial systems are generally available between 2,000 Oe (0.2 T) and 70,000 Oe (7 T). Moreover, the strength of the magnetic field around an MRI may be as high as 300-400 Oe (40 mT) when the MRI is not in use because the superconducting magnets within an MRI machine are generally never turned off And even though MRIs are generally magnetically shielded, the magnetic shielding does not perfectly shield the field generated by the MRI. Thus, the strength of the magnetic fields produced by an MRI (or any other machinery that creates strong magnetic fields) may easily corrupt data in a magnetic-based memory, such as STT-MRAM.

Because an implantable device is not easily removed, a solution is necessary for STT-MRAM to be usable in implantable devices. One solution to the problem of using magnetic-based memories in implantable devices (and other electronic device), which may experience strong magnetic fields, is to offload (e.g., by transferring) data from a magnetic-based memory (e.g., STT-MRAM) to a non-magnetic-based memory (e.g., SRAM) when the implantable device enters a strong magnetic field. However, because the implantable device may not have a native ability to detect the strength of the magnetic field, the implantable device may instead leverage a remote electronic device that is in data communications with the implantable device. In this example, if a first, implanted electronic device receives an indication of a strong ambient magnetic field, e.g., from a second, not-implanted electronic device in data communication with the first electronic device, then the first electronic device may move the data from the magnetic-based memory to a secondary memory prior to the magnetic field reaching a strength that may corrupt the memory. Thus, a process may be undertaken within the first electronic device to preserve the contents of the magnetic-based memory while experiencing a strong magnetic field. Subsequently, when the first electronic device receives an indication that the strong magnetic field has subsided (e.g., via a data transmission from the second electronic device), then the data may be moved back from the second memory to the magnetic-based memory in order to continue utilizing the benefits of the magnetic-based memory (e.g., lower power use).

Example Methods and Systems for Dynamically Protecting Memory

FIG. 1 depicts a method 100 of protecting data in a memory in an electronic device. The method 100 beings at step 102 where data is stored in a first memory in the electronic device, such as an implanted device. The data may be, for example, software, user data, operational data, sensor data, or any other sort of data stored in the electronic device. In some embodiments, the first memory may be a magnetoresistive random-access memory (MRAM), such as a Spin-Transfer Torque (STT) MRAM (STT-MRAM). In some embodiments, the STT-MRAM is a perpendicular magnetic tunnel junction (pMTJ) based STT-MRAM.

The method 100 then proceeds to step 104 where a first indication of a strength of an ambient magnetic field is received from a remote device via a data transmission protocol. For example, the indication may be a numerical indicator of the absolute magnetic field strength (e.g., 1500 Oe), a numerical indicator of a relative strength (e.g., 200% of normal), an ordinal indicator (e.g., "high"), or the like. In some embodiments, the strength of the ambient magnetic field is determined via a magnetic sensor in the remote device, which in some examples is a tunnel-magnetoresistance (TMR) sensor.

In some embodiments, the remote device is a mobile device, such as a smartphone, tablet, smart-wearable device (e.g., smartwatch), or another mobile data device that may be carried by a person having an implanted device. Further, in some embodiments, the transmission protocol may be Bluetooth, Bluetooth Low Energy (BLE), WiFi, Medical Implant Communication Service (MICS), Medical Device Radiocommunications Service (MedRadio), Medical Data Service (MEDS), or other suitable transmission protocols.

The method 100 then proceeds to step 106 where the first indication of the strength of the ambient magnetic field is compared to a threshold. In some embodiments, the threshold may be in the range of 300 to 500 oersted (Oe). For example, the numerical threshold may be 300 Oe, 400 Oe, 500 Oe, or other specific values within the range of 300 to 500 Oe. Other numerical thresholds are possible. For example, the threshold may be higher where the electronic device is capable of withstanding a higher strength magnetic field (e.g., where it is magnetically shielded). In other embodiments, the threshold may be an ordinal threshold, such as "low."

Figure 2:
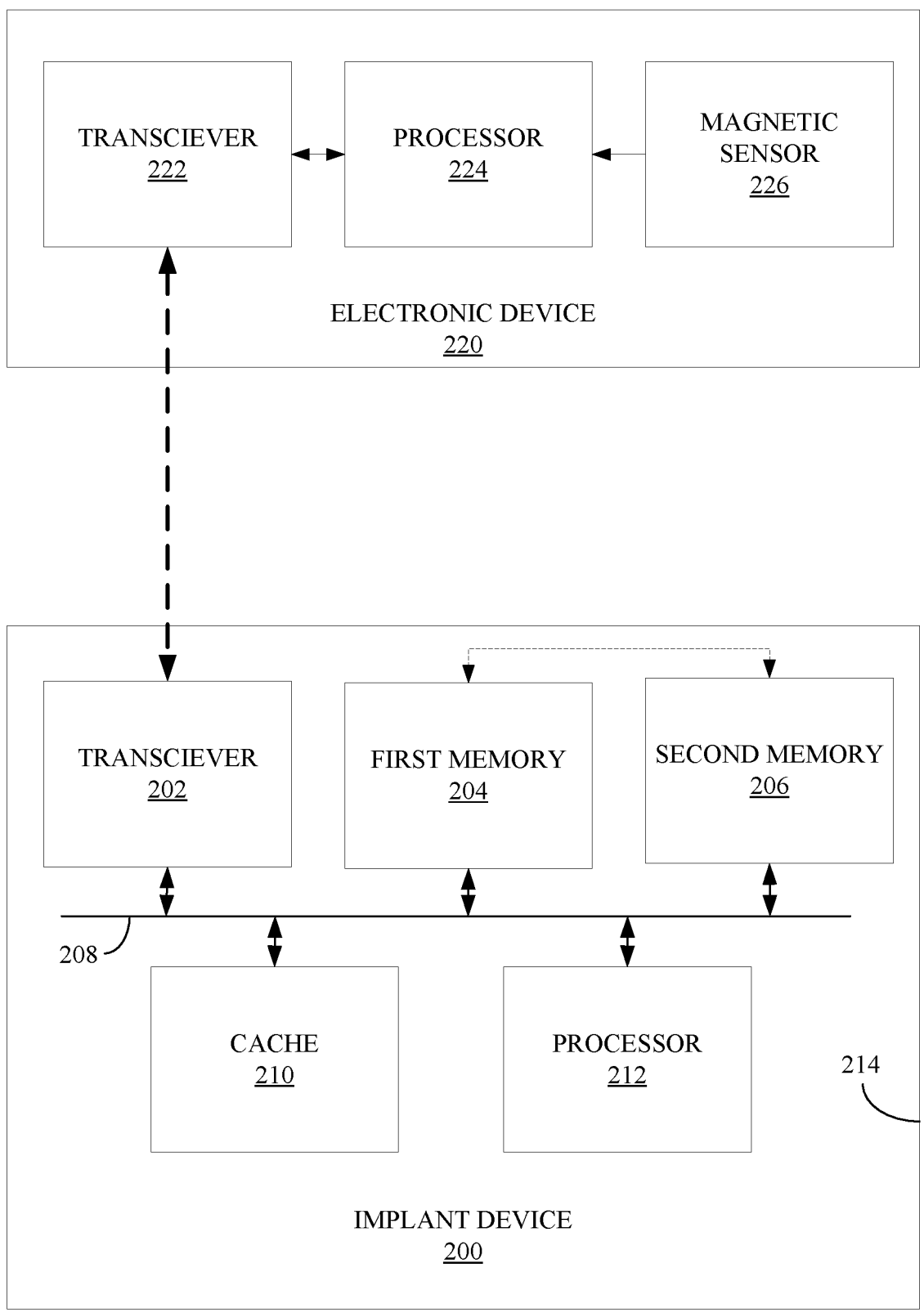
FIG. 2 depicts an electronic device configured to protect data in its memory.

In an alternative embodiment, not depicted in FIG. 2, the remote device may send a memory management instruction via the transmission protocol instead of the first indication of the strength of the ambient magnetic field. Thus, in such an embodiment, the remote device may compare the strength of the ambient magnetic field to the threshold, and, based on that comparison, may send an appropriate memory management instruction. For example, when the remote device determines that the ambient magnetic field strength has exceeded the threshold, the remote device may send an instruction to transfer data in a first memory to a second memory.

The method 100 then proceeds to step 108 where the data in the first memory is transferred to a second memory. As above, this may be in response to determining that the strength of the ambient magnetic field exceeds the threshold (based on the received first indication) or in response to receiving a memory management instruction from the remote device. The data may be moved or copied or otherwise transferred from the first memory to the second memory via a data bus connecting the first memory and the second memory. In some embodiments, the second memory may be a dynamic random-access memory (DRAM), a static random-access memory (SRAM), a flash memory, or any other sort of memory that is resistant to strong magnetic fields. Further, as above, the threshold may be a numerical threshold, such as 450 Oe, or it may be an ordinal threshold, such as "low." Other examples are possible.

The method 100 then proceeds to step 110 where the first memory is disabled. As above, this may be in response to determining that the strength of the ambient magnetic field exceeds the threshold (based on the received first indication) or in response to receiving a memory management instruction from the remote device. For example, the memory may be deactivated or turned off by appropriate circuit elements or it may simply be unmounted or otherwise ignored via firmware or software. In other examples, the first memory may be left enabled, but may not be used (e.g., accessed or stored to) during the time that the ambient magnetic field exceeds the threshold.

The method 100 then proceeds to step 112 where the data is accessed by a processor while the data is stored in the second memory. For example, the processor may continue to execute instructions (e.g., firmware or software) based on the data stored in the second memory while the first memory is disabled or otherwise not being used. In this way, the electronic device is able to continue operating normally while the first memory, which may be a primary memory of the electronic device, is unavailable. The processor may continue to create and store new data to the second memory while the first memory is unavailable. Because the second memory may have to act as a complete backup of the first memory, in some embodiments the second memory is at least the same size as the first memory (i.e., has at least the same capacity). Thus, the electronic device may continue to function normally despite the first memory being unavailable.

The method 100 then proceeds to step 114 where a second indication of a strength of an ambient magnetic field is received from the remote device via the data transmission protocol. As above, the second indication may be an absolute or relative numerical indicator, an ordinal indicator, or any other indicator suitable for making a comparison.

In the alternative embodiment discussed above (not depicted in FIG. 2), the remote device may send a second memory management instruction via the transmission protocol, rather than a second indication of the strength of the ambient magnetic field. For example, if the remote device determines that the ambient magnetic field has crossed below the threshold, the remote device may send an instruction to transfer data back into the first memory from the second memory.

The method 100 then proceeds to step 116 where the second indication of the strength of the ambient magnetic field is compared to the threshold.

The method 100 then proceeds to step 118 where the data is transferred from the second memory to the first memory upon determining that the strength of the ambient magnetic field no longer exceeds the threshold. The data that is transferred back may be the exact same data as transferred to the second memory, or in some cases may be a different set of data. For example, where the electronic device continues to operate normally after the transfer of data, the electronic device may create new data (e.g., operational data) that is stored in the second memory and then subsequently transferred back to the first memory. Thus, the content of the data stored in the second memory may change while the first memory is unavailable and the entire content of the second memory may subsequently be transferred back to the first memory.

Further, in this example, the same threshold triggers transferring the data either to the second memory from the first memory, or back to the first memory from the second memory. However, in some examples more than one threshold may be used (e.g., a transfer out of the first memory threshold and a transfer into the first memory threshold) in order to avoid excessive memory transfer operations when the remote device is located in an area where the magnetic field is fluctuating above and below the threshold, or when the remote device is moving in an out of a threshold level magnetic field. Thus, in some cases the threshold may have hysteresis properties to avoid the unnecessary switching.

FIG. 2 depicts an implant device 200 configured to protect data in its memory. As depicted, implant device 200 is in data communication with a remote electronic device 220. Electronic device 220 may be a mobile device, such as a smartphone, tablet, smart-wearable device (e.g., smartwatch), or other mobile data devices that may be carried by a user in which implant device 200 is implanted. Preferably, electronic device 220 may be a device that is frequently or always carried by the user so that the memory protection methods described herein may always be operating. However, in other embodiments, electronic device 220 may be a fixed electronic device that is installed in proximity to other devices that create strong magnetic fields, such as MRI machines.

Electronic device 220 includes a transceiver 222 configured to carry out wireless communications with other devices, such as implant device 200. In some examples, transceiver 222 may be operative to transmit and receive data via one or more transmission protocols, such as those described above (including: Bluetooth, Bluetooth Low Energy (BLE), WiFi, Medical Implant Communication Service (MICS), Medical Device Radiocommunications Service (MedRadio), Medical Data Service (MEDS), or other suitable transmission protocols.

Electronic device 220 includes a magnetic sensor 226. Magnetic sensor 226 may be any sort of magnetometer or magnetoresistive transducers that may measure at least the strength of a magnetic field, and may additionally be capable of measuring the direction or relative change of a magnetic field at a particular location. In some embodiments, magnetic sensor 226 may be a Hall Effect sensor, an anisotropic magnetoresistance (AMR) sensor, a giant magnetoresistance (GMR) sensor, a tunneling magnetoresistance (TMR) sensor, or other types of magnetic sensor. Note that term magnetic tunnel junction (MTJ) may be used to refer to a TMR sensing element.

A TMR sensor may be a preferred sensor for electronic device 220. Relative to a Hall Effect sensor, a TMR sensor has better temperature stability, higher sensitivity, lower power consumption, better linearity, and needs no additional flux concentrator structure. Relative to an AMR sensor, a TMR sensor has better temperature stability, higher sensitivity, and a wider linear range. And relative to a GMR sensor, a TMR sensor has better temperature stability, higher sensitivity, lower power consumption, and a wider linear range. Further, a TMR sensor generally has the smallest die size of all the aforementioned sensor types. This characteristic is particularly important for implantable electronic devices since space is very limited in such applications.

Generally, a TMR sensing element may include a pinned ferromagnetic layer, a tunnel barrier layer, and a free ferromagnetic layer. The pinned ferromagnetic layer may be a composite layer formed of an anti-ferromagnetic pinning layer and a ferromagnetic layer. Or the pinned layer could be an alloy with high coercivity. The tunnel barrier layer is generally made of MgO or AlOx. The ferromagnetic layer is "free" because there is no "pinning layer" as there is with the pinned ferromagnetic layer. The pinned layer magnetization direction is relatively fixed in the presence of modest magnetic fields. The free layer magnetization direction is relatively easy to rotate in modest magnetic fields. The TMR sensing element may further include a bottom conducting layer and a top conducting layer that are in direct electrical contact with the anti-ferromagnetic layer, and the free layer, respectively. The top and bottom conductive (i.e., electrode) layers may be formed of a non-magnetic conductive material and may carry input current through the tunnel junction and to meters that measure the current (or voltage). The bottom conducting layer may be supported by an insulating layer. Further, a substrate may be located beneath all of the other layers.

Electronic device 220 also includes a processor 224. Processor 224 may be any sort of processor capable of executing executable instructions. For example, processor 224 may be configured to receive magnetic sensor data from magnetic sensor 226 and construct an indication of the strength of the ambient magnetic field for transmission to implant device 200 via transceiver 222. In some examples, the indication may be sent by way of a transmission protocol, such as those described above. In some examples, the indication may be encapsulated in a standard data format, such as an IP packet or the like.

In some embodiments, electronic device 220 may also compare the magnetic sensor data from magnetic sensor 226 to a threshold. In such examples, if the strength of the magnetic field exceeds the threshold, electronic device 220 may transmit an memory management instruction to implant device 200 via transceiver 222, wherein the instruction is configured to cause implant device 200 to transfer data in a first, magnetic field-sensitive memory to a second, magnetic field-insensitive memory. Conversely, if the strength of the magnetic falls below the threshold, electronic device 220 may transmit another memory management instruction to implant device 200 via transceiver 222, wherein the instruction is configured to cause the implant device transfer data from the second, magnetic field-insensitive memory back into the first, magnetic field-sensitive memory from the second, magnetic field-insensitive memory.

Notably, electronic device 220 is depicted only with features (e.g., transceiver 222, processor 224, and magnetic sensor 226) relevant to the particular methods described herein. Electronic device 220 may have many additional features, such as, for example, a display, one or more memories, sound capturing devices, sound emitting devices, other types of sensors, etc.

Implant device 200 includes a transceiver 202, which is configured to carry out wireless communications with other devices, such as electronic device 220. In some examples, transceiver 202 may be operative to transmit and receive data via one or more transmission protocols, as discussed above.

Implant device 200 also includes a first memory 204. As discussed above with respect to FIG. 1, in some embodiments, the first memory may be a magnetic-based memory. For example, the first memory may be a STT-MRAM, such as a PMTJ-based STT-MRAM. In other embodiments, the first memory may be a ferroelectric RAM (e.g., FeRAM, F-RAM, or FRAM).

Implant device 200 also includes a second memory 206. As discussed above with respect to FIG. 1, in some embodiments, the second memory may be non-magnetic-based memory. For example, the second memory may be a volatile memory, such as dynamic random-access memory (DRAM), a double data rate synchronous dynamic random-access memory (DDR SDRAM), a static random-access memory (SRAM), a quad data rate (QDR) SRAM, and others. Or the second memory may be a non-volatile memory, such as non-volatile random-access memory (NVRAM) (e.g., flash memory), non-volatile SRAM (nvS-RAM), phase-change memory (e.g., PRAM), conductive-bridging RAM (CBRAM), resistive random-access memory (RRAM or ReRAM), Nano-RAM (NRAM), and others.

Implant device 200 also includes cache 210. Cache 210 may be, for example, a memory reserved for use of processor 212 to process data and move data. For example, as described above, the data within first memory 204 may be moved to second memory 206 when implant device 200 receives an indication of a strong ambient magnetic field or an appropriate memory management instruction. In some examples, the contents may be moved between memories by way of cache 210. In other examples, cache 210 may simply be a high-speed local working memory for use by processor 212.

Implant device 200 also includes processor 212. Processor 212 may be any sort of processor capable of executing executable instructions. For example, processor 212 may be configured to perform the steps described with respect to FIG. 1, above. By way of example, processor 212 may receive from electronic device 220 via transceiver 202 (and an appropriate transmission protocol), a first indication of a strength of an ambient magnetic field and may compare the indication to a threshold. If the strength of the magnetic field exceeds the threshold, processor 212 may initiate a transfer of data from first memory 204 to second memory 206. In some examples, the transfer may be directly between first memory 204 and 206 via common data bus 208. In other examples, processor 212 may use cache 210 while transferring data from first memory 204 to second memory 206. In yet other examples, a dedicated data channel may run between first memory 204 and second memory 206 (as depicted by the broken line between the two), which facilitates rapid transfer of the data between the two memories without the normal contention on data bus 208.

In an alternative embodiment, implant device 200 may receive from electronic device 220 via transceiver 202 (and an appropriate transmission protocol), an instruction regarding management of first memory 204 and second memory 206. For example, implant device 200 may receive an instruction that causes processor 212 to transfer data in first memory 204 to second memory 206. Implant device 200 may also receive an instruction that causes processor 212 to transfer data back into first memory 204 from second memory 206.

Implant device 200 also includes data bus 208, which may provide a data connection between all aspects of implant device 200. Though shown as a single data bus in FIG. 2, implant device 200 may include a plurality of data buses.

Implant device 200 may also include a housing 214. The housing may envelop transceiver 202, first memory 204, second memory 206, data bus 208, cache 210, and processor 212, among other things. In some embodiments, housing 214 may be a bio-compatible substances, such as certain plastics, polymers, or metals that may be implanted within a body. For example, bio-compatible plastics may include polyvinylchloride, polyethersulfone, polytetrafluoroethylene, polyethylene, polyurethane, polyetherimide, polycarbonate, polysulfone, polyetheretherketone, polypropylene, and others. Biocompatible plastics may include, for example, stainless steel, CoCr alloys, Ti alloys, and others.

Figure 3:
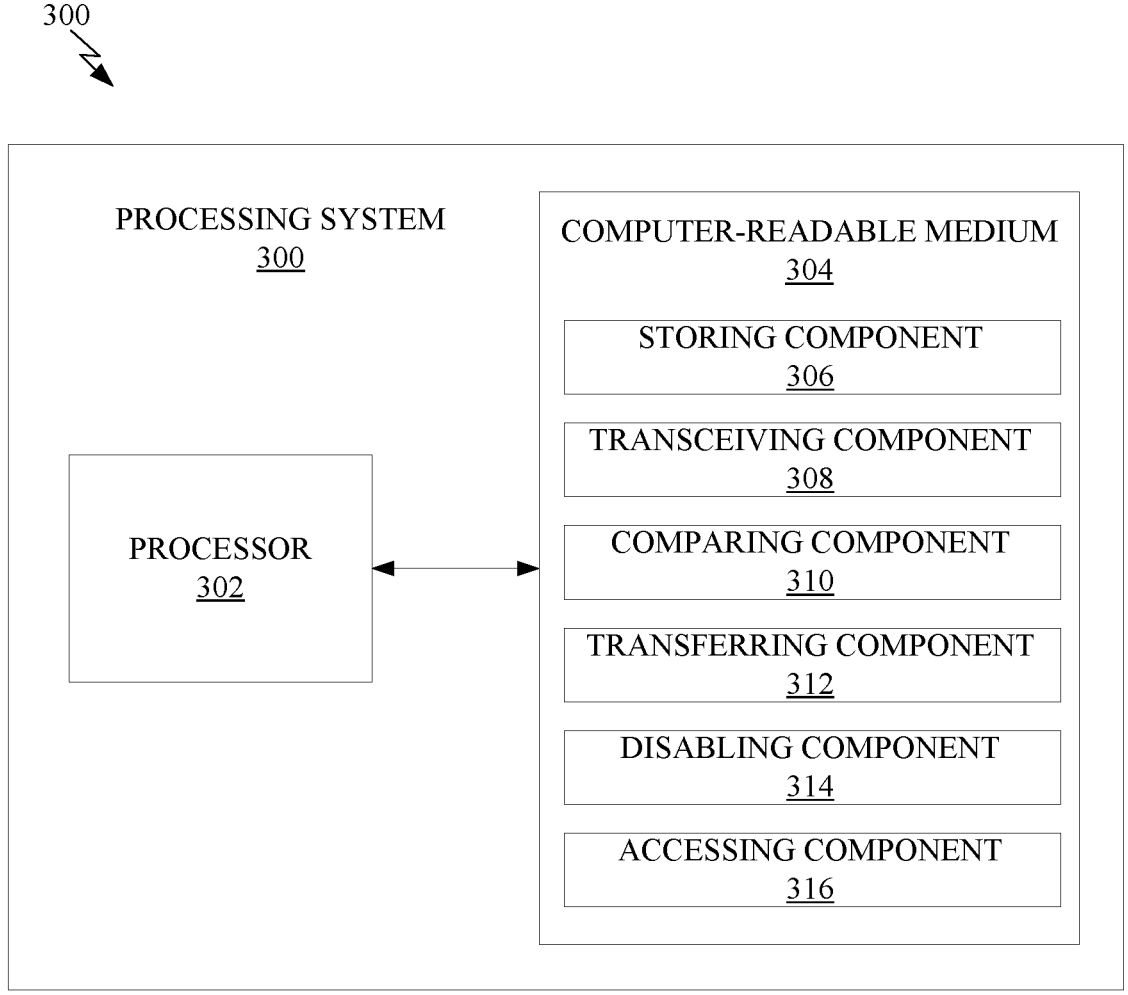
FIG. 3 depicts an example processing system.

FIG. 3 depicts an example processing system 300 configured to perform aspects described herein. Processing system 300 includes a processor 302 in data communication with a computer-readable medium 304. Computer-readable medium 304 includes a variety of components, including a storing component 306, a transceiving component 308, a comparing component 310, a transferring component 312, a disabling component 314, and an accessing component 316. Notably, in other embodiments, computer-readable medium 304 may include more or fewer components.

Storing component 306 may be configured to or otherwise provide a means to, for example, store data in one or more memories, such as described above with respect to FIG. 1.

Transceiving component 308 may be configured to or otherwise provide a means to, for example, wirelessly transmit or receive data (e.g., via a data transmission protocol) from other devices, such as described above with respect to FIG. 1.

Comparing component 310 may be configured to or otherwise provide a means to, for example, compare a determined strength of the magnetic field to a threshold, such as described above with respect to FIG. 1.

Transferring component 312 may be configured to or otherwise provide a means to, for example, transfer data from at least a first memory to at least a second memory, such as described above with respect to FIG. 1.

Disabling component 314 may be configured to or otherwise provide a means to, for example, disable a memory of an electronic device, such as described above with respect to FIG. 1.

Accessing component 316 may be configured to or otherwise provide a means to, for example, access data stored in one or more memories, such as described above with respect to FIG. 1.

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method of protecting data in a magnetic random access memory (MRAM), comprising:
   storing data in a first memory of a first device;
   receiving, from a second device via a wireless data transmission protocol, a first indication of an intensity of an ambient magnetic field measured by a magnetic sensor of the second device;
   comparing the first indication of the intensity of the ambient magnetic field to a threshold;
   transferring the data in the first memory of the first device to a second memory of the first device upon determining that the first indication of the intensity of the ambient magnetic field exceeds the threshold;
   receiving, from the second device via the wireless data transmission protocol, a second indication of the intensity of the ambient magnetic field measured by the second device;
   comparing the second indication of the intensity of the ambient magnetic field to the threshold; and
   transferring the data from the second memory of the first device to the first memory of the first device upon determining that the second indication of the intensity of the ambient magnetic field no longer exceeds the threshold.

2. The method of claim 1, wherein the first memory is a magnetoresistive random-access memory (MRAM).

3. The method of claim 2, wherein the second memory is a static random access memory (SRAM).

4. The method of claim 3, wherein the magnetic sensor is a tunnel-magnetoresistance (TMR) sensor.

5. The method of claim 4, wherein the first memory is a Spin-Transfer Torque (STT) MRAM.

6. The method of claim 4, wherein the threshold is in a range of 300 to 500 oersted (Oe).

7. The method of claim 1, wherein the wireless data transmission protocol is one of: Bluetooth Low Energy (BLE), WiFi, Medical Implant Communication Service (MICS), Medical Device Radiocommunications Service (MedRadio), or Medical Data Service (MEDS).

8. The method of claim 1, further comprising: disabling the first memory upon determining that the intensity of the ambient magnetic field exceeds the threshold.

9. The method of claim 1, further comprising: transmitting, to remote device via the wireless data transmission protocol, an indication that the data has been moved from the first memory to the second memory.

10. An electronic device, comprising:
a first memory;
a second memory;
a transceiver; and
a processor in data communication with the first memory, the second memory, and the transceiver and configured to:
store data in the first memory;
receive, from a remote device via the transceiver using a wireless data transmission protocol, a first indication of an intensity of an ambient magnetic field measured by a magnetic sensor of the remote device;
compare the first indication of the intensity of the ambient magnetic field to a threshold;
transfer the data in the first memory to second memory upon determining that the first indication of the intensity of the ambient magnetic field exceeds the threshold;
receive, from the remote device via the transceiver using the wireless data transmission protocol, a second indication of the intensity of the ambient magnetic field measured by the magnetic sensor of the remote device;
compare the second indication of the intensity of the ambient magnetic field to the threshold; and
transfer the data from the second memory to the first memory upon determining that the second indication of the intensity of the ambient magnetic field no longer exceeds the threshold.

11. The electronic device of claim 10, wherein the first memory is a magnetoresistive random-access memory (MRAM).

12. The electronic device of claim 11, wherein the second memory is a static random access memory (SRAM).

13. The electronic device of claim 12, wherein the magnetic sensor is a tunnel-magnetoresistance (TMR) sensor.

14. The electronic device of claim 13, wherein the first memory is a Spin-Transfer Torque (STT) MRAM.

15. The electronic device of claim 13, wherein the threshold is in a range of 300 to 500 oersted (Oe).

16. The electronic device of claim 10, wherein the wireless data transmission protocol is one of: Bluetooth Low Energy (BLE), WiFi, Medical Implant Communication Service (MICS), Medical Device Radiocommunications Service (MedRadio), or Medical Data Service (MEDS).

17. The electronic device of claim 10, wherein the processor is further configured to: disable the first memory upon determining that the intensity of the ambient magnetic field exceeds the threshold.

18. The electronic device of claim 10, further comprising a housing enveloping the first memory, the second memory; and the processor, wherein the housing is configured to be implanted in a human body.

19. A non-transitory, computer-readable medium comprising instructions that, when executed by a processor of a first device, cause the first device to perform a method of protecting data in a memory in an electronic device, the method comprising:
storing data in a first memory of the first device;
receiving, from a second device via a wireless data transmission protocol, a first indication of an intensity of an ambient magnetic field measured by the second device;
comparing the first indication of the intensity of the ambient magnetic field to a threshold;
transferring the data in the first memory of the first device to a second memory of the first device upon determining that the first indication of the intensity of the ambient magnetic field exceeds the threshold;
receiving, from the second device via the wireless data transmission protocol, a second indication of the intensity of the ambient magnetic field measured by the second device;
comparing the second indication of the intensity of the ambient magnetic field to the threshold; and
transferring the data from the second memory of the first device to the first memory of the first device upon determining that the second indication of the intensity of the ambient magnetic field no longer exceeds the threshold.

20. The non-transitory, computer-readable medium of claim 19, wherein the first memory is a Spin-Transfer Torque (STT) MRAM.

* * * * *